US005744167A

United States Patent [19]

Majeti

[11] Patent Number: 5,744,167
[45] Date of Patent: Apr. 28, 1998

[54] METHODS FOR THE TREATMENT OF HERPES VIRUS INFECTIONS

[75] Inventor: Satyanarayana Majeti, Cincinnati, Ohio

[73] Assignee: The Procter & Gamble Company, Cincinnati, Ohio

[21] Appl. No.: 779,787

[22] Filed: Jan. 7, 1997

Related U.S. Application Data

[62] Division of Ser. No. 654,952, May 29, 1996, Pat. No. 5,658,946.

[51] Int. Cl.$^6$ .......................... A61K 31/32; A61K 31/19; A61K 33/24

[52] U.S. Cl. .......................... 424/650; 514/493; 514/557; 514/574; 514/931; 514/934

[58] Field of Search .......................... 514/493, 934, 514/557, 574, 931; 424/650

[56] References Cited

U.S. PATENT DOCUMENTS

| | | | |
|---|---|---|---|
| 4,383,990 | 5/1983 | Coe et al. | 424/180 |
| 4,902,497 | 2/1990 | Crisanti et al. | 424/52 |
| 5,004,597 | 4/1991 | Majeti et al. | 424/52 |
| 5,098,716 | 3/1992 | Embro | 424/650 |

FOREIGN PATENT DOCUMENTS

RO 75422  1/1981  Romania .

WO 93/25211  12/1993  WIPO .

OTHER PUBLICATIONS

Doolittle, et al., "Inactivation of Bacteriophage T4 by Organic and Inorganic Tin Compounds", Journal of Industrial Microbiology, 10 (1992), pp. 221–228.

Tallberg, T., et al., "Equine Sarcoid Successfully Treated by Bio–Immunotherapy", Dtsch. Z Onkol. (1994), 28/2, pp. 34–40.

*Primary Examiner*—John Pak
*Attorney, Agent, or Firm*—Angela Marie Stone; Mary Catherine Hentz; Douglas C. Mohl

[57] ABSTRACT

Disclosed are methods for treatment of herpes virus infections in a human or lower animal subject comprising administering to the subject stannous salt and one or more pharmaceutically acceptable carriers suitable for topical administration. The stannous salt may be one or more stannous carboxylates, a stannous halide selected from the groups consisting of stannous bromide, stannous iodide, and stannous chloride dihydrate, two or more stannous halides, or one or more stannous halides and one or more stannous carboxylates. Another therapeutic agent, such as an anesthetic, analgesic, or antibiotic, may also be administered. Also disclosed are compositions effective in treating herpes virus infections in a human or lower animal subject comprising stannous fluoride, one or more therapeutic agents, and one or more pharmaceutically acceptable carriers suitable for topical administration.

3 Claims, No Drawings

5,744,167

METHODS FOR THE TREATMENT OF HERPES VIRUS INFECTIONS

This is a division of application Ser. No. 08/654,952, filed on May 29, 1996 which is now U.S. Pat. No. 5,658,946.

BACKGROUND OF THE INVENTION

Herpetic inflections are highly contagious skin eruptions or lesions, characterized by a cluster of small blisters or watery vesicles. The lesions are caused by an acute vital infection. The virus is from the genus Herpesvirus.

There are several types of viruses in the genus Herpesvirus. Two commonly known viruses are herpes types 1 and 2, referred to as HSV1 and HSV2. HSV1 causes orofacial lesions, commonly known as fever blisters or cold sores. These lesions most commonly appear on the lips, but may appear on the face, in the mucous membrane lining of the oral cavity, in the eye, and occasionally on the trunk or hands. Approximately 30% of the U.S. population suffers from recurrent episodes of HSV1. HSV2, which is less common than HSV1, causes genital lesions. Kirk & Othmer, *Encyclopedia of Chemical Technology*, Fourth Edition, Volume 3, Wiley-Interscienee Publishers (1992), pp. 576–583.

Other types of Herpesvirus infections are caused by the varicella-zoster virus. The varicella-zoster virus causes varicella, commonly known as chicken pox, and herpes zoster, commonly known as shingles. Shingles affects the skin and nerves and is characterized by groups of small blisters or lesions appearing along certain nerve segments. The lesions are most often seen on the back and may be preceded by a dull ache in the affected site. Id.

There is no treatment known to kill the herpes virus. Therefore, the virus may remain in some latent form in the skin. Because there is no known treatment to kill the herpes virus or effectively prevent outbreaks of the lesions, recurrent herpes virus infections are common. Currently, the most commonly prescribed treatment of herpes virus infections is Zovirax® Ointment which contains the active ingredient acyclovir. Common over the counter treatments for herpes virus infections include Zilactin® Medicated Gel, Tanac® Medicated Gel, Orajel® Mouth-Aid, and Herpecin-L® Cold Sore Lip Balm. These treatments aid in helping to speed the healing of the lesions and the associated symptoms, but have not been shown to be efficacious in the treatment of herpes virus infections. Stannous fluoride has also been disclosed as a method for treating diseases having vital etiology. U.S. Pat. No. 5,098,716, issued Mar. 24, 1992, and International Publication No. WO 93/25211, published Dec. 23, 1993, to Embro disclose the use of stannous fluoride to treat herpes virus infections. However, the need still exists for new alternatives for treating herpes virus infections.

It has been discovered by the present invention that the topical administration of various stannous salts or stannous fluoride in combination with other stannous salts are effective for treating herpes infections and lesions. It has also been discovered that the topically-administered stannous salt compositions may also contain another therapeutic agent, such as an anesthetic, analgesic, or antibiotic. The topical application of these compositions will help to control the growth of the herpes virus, reduce the severity of the infection, and aid in reducing or eliminating the pain, redness, inflammation, and itching caused by the herpetic infections.

It is an object of the present invention to provide safe and effective methods for the treatment of herpes virus infections comprising the topical administration of various stannous salts or stannous fluoride in combination with other stannous salts. It is also an object of present invention to provide safe and effective methods and compositions which additionally contain another therapeutic agent. It is also an object of the present invention to provide a method comprising administering a stannous composition which helps to control the growth of the herpes virus, reduce the severity of the infection, and aid in reducing or eliminating the pain, redness, inflammation, and itching caused by the herpetic infections.

These and other objects of the present invention will become readily apparent from the detailed description which follows.

All percentages and ratios used herein are by weight of the total composition, and all measurements are made at 25° C., unless otherwise specified.

SUMMARY OF THE INVENTION

The present invention relates to a method for treatment of herpes virus infections in a human or lower animal subject comprising administering to the subject a safe and effective mount of one or more stannous carboxylates and one or more pharmaceutically acceptable carriers suitable for topical administration.

The present invention also relates to a method for treatment of herpes virus infections in a human or lower animal subject comprising administering to the subject a safe and effective mount of a stannous halide selected from the group consisting of stannous bromide, stannous iodide, and Stannous chloride dihydrate, or a safe and effective amount of two or more stannous halides, and one or more pharmaceutically acceptable carriers suitable for topical administration.

The present invention also relates to a method for treatment of herpes virus infections in a human or lower animal subject comprising administering to the subject a safe and effective mount of one or more stannous halides, a safe and effective amount of one or more stannous carboxylates, and one or more pharmaceutically acceptable carriers suitable for topical administration.

The present invention also relates to a composition effective in treating herpes virus infections in a human or lower animal subject comprising a safe and effective amount of stannous fluoride, a safe and effective mount of one or more therapeutic agents, and one or more pharmaceutically acceptable carriers suitable for topical administration.

DETAILED DESCRIPTION OF THE INVENTION

The present invention relates to a method for treatment of herpes virus infections. The phrase "treatment of herpes virus infections" as used herein includes helping to control the growth of the virus and aiding in reducing or eliminating the pain, redness, inflammation, and itching caused by the herpetic infection. The compositions used to treat the herpes virus infectious comprise various stannous salts or stannous fluoride in combination with another stannous salt. These compositions can also include another therapeutic agent. The composition of the present invention may be in the form of a lotion, ointment, cream, or other form suitable for topical administration.

The term "safe and effective amount" as used herein means a sufficient amount of material that is safe to the skin and helps to control the growth of the herpes virus, reduce the severity of the infection, and aid in reducing or eliminating the associated pain, redness, inflammation, and itching of the herpetic infections.

The term "stannous salt" as used herein means any stannous compound suitable for application to the skin. The stannous salt may be organic, such as a stannous carboxylate, or inorganic, such as a stannous halide.

The term "pharmaceutically acceptable carrier" as used herein means any suitable vehicle which is safe for human use, does not interfere with the stannous salt utilized, and can be applied to the skin. Such vehicles include emollients, skin conditioning agents, penetration enhancers, sun screening agents, purified water, solvents, preservatives, thickeners, humectants, dyes, opacifiers, pigments, flavor oils, perfumes and other materials.

The term "therapeutic agent" as used herein means an anesthetic, analgesic, antibiotic, or other suitable substance with a medicinal effect. The analgesics include steroidal and non-steroidal anti-inflammatory agents.

The essential, as well as optional components, of the methods of treatment of herpes virus infections according to the present invention are described in the following paragraphs.

Stannous Salts

The method of treatment in the present invention includes administration of one or more stannous salts. The stannous salts that may be used include organic stannous carboxylates and inorganic stannous halides. The preferred organic stannous carboxylates are formed from mono-, di-, or tri- alpha hydroxy containing carboxylic acids and alpha amino carboxylic acids. Suitable carboxylic acids for this invention include but are not limited to: gluconic, acetic, tartaric, lactic, glycine, benzoic, maleic, and salicylic among many others. Other suitable carboxylic acids include formic, propionic, butyric, valeric, caproic, enanthic, and capric. The resulting stannous carboxylates include but are not limited to: stannous gluconate, stannous acetate, stannous tartrate, stannous malonate, stannous citrate, stannous ethylene glycoxide, and stannous formate among others.

Several stannous halide salts are also suitable for this invention. Halides that may be used to form stannous salts include fluoride, chloride, bromide and iodide. The resulting stannous halides include but are not limited to: stannous fluoride, stannous chloride, stannous chloride dihydrate, stannous bromide, and stannous iodide among others. While stannous fluoride may be used, it is used only in combination with another stannous halide or one or more stannous carboxylates or another therapeutic agent.

The stannous salts are described in detail in Kirk & Othmer, *Encyclopedia of Chemical Technology*, Third Edition, Volume 23, Wiley-Interscience Publishers (1982), pp. 42–71, incorporated herein by reference in its entirety. The stannous salt is administered at a level of from about 0.05% to about 10%, preferably from about 0.1% to about 8%, most preferably from about 0.2% to about 6% of the final composition.

Therapeutic Agents

The present invention may also include the administration of one or more other therapeutic agents. The therapeutic agent may be an anesthetic, analgesic, antibiotic, or other suitable agent which aids in reducing or eliminating pain, redness, inflammation, and itching associated with the herpetic infections.

Anesthetics useful in this invention include local anesthetics suitable for topical application. These agents are used to reversibly block impulse conduction in peripheral nervous tissue, thereby producing a transient loss of sensation in a circumscribed area of the body. This action will block a sensation of pain. *Remington's Pharmaceutical Sciences*, Eighteenth Edition, MACK Publishing Company (1990), pp. 1048–1056. The anesthetic may be soluble or slightly soluble. A slightly soluble local anesthetic will likely have slow absorption which may produce a less complete but longer anesthetic effect, as compared to a a soluble anesthetics. Salts and base form of several esters and amides are used to produce topical anesthetic. The salts do not penetrate intact skin, but will penetrate abraded or raw granulated skin surfaces. The base forms relieve surface pain, burning, and itching on intact skin. Suitable anesthetics for topical application include: benzocaine, dibucaine, lidocaine, pramoxine hydrochloride, tetracaine, tetracaine hydrochloride, benzyl alcohol, butacaine, butamben picrate, dyclonine, tripelennamine and combination thereof. Anesthetics suitable for topical compositions are described in detail in *Remington's Pharmaceutical Sciences*, Eighteenth Edition, MACK Publishing Company (1990), pp. 1048–1056, which is incorporated herein by reference in its entirety. The anesthetic typically is administered at a level of from about 0.05% to about 30%, preferably from 0.1% to about 20%, and most preferably from about 0.5% to about 10% of the final composition.

Another therapeutic agent is an analgesic. Included in the analgesic group are anti-inflammatory agents. Analgesics are agents which relieve pain by acting centrally to elevate pain threshold without disturbing consciousness or altering other sensory modalities. Analgesics suitable for this topically applied composition include: acetaminophen, sodium salicylate, and trolamine salicylate. Analgesics suitable for topical administration are described in more detail in *Remington's Pharmaceutical Sciences*, Eighteenth Edition, MACK Publishing Company (1990), pp. 1097–1122, which is incorporated herein by reference in its entirety.

Steroidal and nonsteroidal anti-inflammatory agents are also suitable analgesics. Suitable steroidal anti-inflammatory agents include the corticosteroids. Corticosteroids have been found to be highly effective in the management of a large number of acute and chronic lesions of the mouth. A commonly used corticosteroid is fluocinolone. Additionally, hydrocortisone, which is an adrenal hormone, has both anti-inflammatory and anti-itching properties. The nonsteroidal anti-inflammatory groups of analgesic agents may be utilized. Suitable nonsteroidal anti-inflammatory agents including the oxicams, salicylates, and fenamates. Additionally included are choline salicylate, ketoprofen, ketorolac, aspirin, difluisal, ibuprofen, naproxen, and diclofenac. A more complete disclosure of anti-inflammatory agents can be found in U.S. Pat. No. 5,118, 707, Chatterjee et al., issued Jun. 2, 1992, incorporated herein by reference in its entirety.

The exact mount of analgesic to be administered will depend on the particular analgesic to be used as analgesics vary widely in potency. Typically, the analgesic is administered at a level of from about 0.05% to about 30%, preferably from 0.1% to about 20%, and most preferably from about 0.5% to about 10% of the final composition.

The present invention may also include antibiotics suitable for topical application. The antibiotic will help to prevent secondary bacterial infections. Antibiotics suitable for topical application include the polypeptides such as bacitracin, bacitracin zinc, colistin sulfate, polymyxin B sulfate, and others. Antibiotics are described in detail in *Remington's Pharmaceutical Sciences*, Eighteenth Edition, MACK Publishing Company (1990), pp. 1181–1224, which is incorporated herein by reference in its entirety. The antibiotic is administered at a level of from about 0.05% to about 20% and preferably from about 0.5% to about 10% of the final composition.

Pharmaceutically Acceptable Carriers

In preparing the present compositions for topical administration, it is desirable to add one or more pharmaceutically acceptable carriers suitable for topical administration. Such materials are well known in the art and are readily chosen by one skilled in the art based on the physical, aesthetic, and therapeutic properties desired for the topical compositions being prepared. Pharmaceutically acceptable carriers typically are administered at a level of from about 60% to about 99.95%, preferably from about 75% to about 99% of the final composition.

The present compositions are for topical administration and can be in the form of a lotion, cream, ointment or other form that may be applied to the skin. Topical administration is used to deliver a drug at, or immediately beneath, the point of application. Percutaneous absorption occurs mainly from the surface. When the skin is diseased or abraded, the cutaneous barrier may be disrupted or defective, so that percutaneous absorption may be increased.

An optional component in the topical compositions is an emollient. Emollients are bland, fatty or oleaginous substances which may be applied to the skin to help protect the skin from airborne bacteria and possible irritants. The emollient may be used to aid penetration as it softens the skin making it more pliable. Emollients are described in detail in *Remington's Pharmaceutical Sciences*, Eighteenth Edition, MACK Publishing Company (1990), pp. 757–773, which is incorporated herein by reference in its entirety. Emollients can be administered at a level of from about 0.5% to about 2.0% of the final composition.

A skin conditioning agent, such as allantoin, may also be included in the present compositions. Allantoin is used topically as a vulnerary to stimulate tissue repair. Allantoin and other skin conditioning agents are described in detail in *Remington's Pharmaceutical Sciences*, Eighteenth Edition, MACK Publishing Company (1990), pp. 757–773, which is incorporated herein by reference in its entirety. Allantoin can be administered at a level from about 0.1% to about 4.0% and preferably from 0.25% to about 1.0% of the final composition.

A penetration enhancer may also be used in the present invention. A penetration enhancer is a substance that facilitates absorption through the skin. Suitable penetration enhancers include several solvents such as water, methanol, ethanol, alkyl methyl sufoxides, pyrrolidones, and acetone. Additionally, surfactants, others alcohols, fatty acids, and other substances may be used as penetration enhancers in the present compositions. Penetration enhancers are described in detail in *Remington's Pharmaceutical Sciences*, Eighteenth Edition, MACK Publishing Company (1990), pp. 757–773, which is incorporated herein by reference in its entirety. The penetration enhancer generally is administered at a level of from about 0.5% to about 10% of the final composition.

A sun screening agent may additionally be included in the present invention. It is thought that exposure to the sun may trigger a herpes virus infection, therefore a sun screening agent may help to prevent possible recurrent outbreaks of herpes virus infections. A wide variety of conventional sun screening agents are suitable for use in combination with the stannous salts. Specific suitable sun screening agents include p-aminobenzoic acid, anthranilates, salicylates, cinnamic acid derivatives, hydrocarbons, and many others. Additional sun screening agents are described in detail in Chatterjee et al., 5,118,707, Jun. 2, 1992, which is incorporated herein by reference in its entirety. Generally, the sun screening agent is administered at a level of from about 1% to about 20% and preferably from about 2% to about 10% of the final composition.

Other pharmaceutically acceptable carriers may optionally be included in the present compositions. Pharmaceutically acceptable carriers include purified water, solvents, preservatives, thickeners, humectants, dyes, opacifiers, pigments, flavor oils, and perfumes among others. Examples of specific pharmaceutically acceptable carriers include glycerin, white wax, petrolan, stearyl alcohol, propylene glycol, sodium lauryl sulfate, propyl paraben, methyl paraben, and peppermint oil among others.

The present compositions can be in the form of a lotion, cream, ointment, or other form that may be applied to the skin. A lotion is a liquid suspension or dispersion that is used for topical application to the skin. It is prepared by forming a smooth paste with the ingredients and then adding the remaining liquid ingredients. Another suitable form for the present composition is an ointment. An ointment is a semisolid composition intended for external application to the skin or mucous membranes. The ointment properties may vary to allow for specific uses, ease of application, or extent of application. The ointment base may be a hydrocarbon, absorption, emulsion, or water-soluble base. Lanolin is commonly used as a vehicle for ointments because of its compatibility with skin lipids. Another suitable form for the present composition is a cream, which is classified as type of ointment. The cream is a viscous liquid or semisolid emulsion.

The present compositions may be non-aqueous or aqueous. It is preferred that the composition be non-aqueous if the composition additionally contains a therapeutic agent. Non-aqueous and aqueous compositions should be substantially free from di- and multi-valent metal ions such as aluminum, magnesium, iron, and calcium. In the aqueous composition, the composition should also be substantially free from chelating agents, specifically those that are multi-valent anions capable of forming an insoluble complex with the stannous ions. Such chelating agents include titrate, phosphate, pyrophosphate, phytate, and tartate.

The pH of the compositions should be a pH which is safe for application to the skin and will provide optimal effect of the stannous salts. Such pH's are from about 3.5 to about 8, preferably from about 5 to about 7.

METHOD OF USE

The present invention comprises methods for treatment of herpes virus infection in a human or lower animal subject comprising administering to the subject one of the present invention compositions. The method of treatment herein comprises topically applying the composition to the herpetic infection. The composition may be applied with a cotton swap or other sterile implement. A sufficient mount of the composition to cover the herpetic infection should be applied. The composition should be applied as often as needed until the condition has totally cleared. Usually, the composition will be applied from seven to twenty-one days. In reoccurring situations, the composition may be applied prior to an eruption, at the first sign of an eruption. Common signs include tenderness, itching, and tingling sensations.

METHOD OF MANUFACTURE

The carrier compositions of the present invention can be made using methods which are common in the industry.

Methods of manufacture for topical compositions are described in detail in *Remington's Pharmaceutical Sciences*, Eighteenth Edition, MACK Publishing Company (1990), pp. 1538-1544 and pp. 1602-1609, which is incorporated herein by reference in its entirety.

The following examples further describe and demonstrate preferred embodiments within the scope of the present invention. The examples are given solely for illustration and are not to be construed as limitations of this invention as many variations thereof are possible without department from the spirit and scope thereof.

EXAMPLE 1

| Component | Percent by Weight |
| --- | --- |
| Stannous fluoride | 0.45 |
| Stannous gluconate | 3.00 |
| White wax | 5.00 |
| Petrolatum | 91.54 |
| Peppermint oil | 0.01 |

EXAMPLE 2

| Component | Percent by Weight |
| --- | --- |
| Stannous gluconate | 3.00 |
| White wax | 5.00 |
| Petrolatum | 91.99 |
| Peppermint oil | 0.01 |

EXAMPLE 3

| Component | Percent by Weight |
| --- | --- |
| Stannous fluoride | 0.45 |
| Benzocaine | 5.00 |
| White wax | 5.00 |
| Petrolatum | 89.54 |
| Peppermint oil | 0.01 |

EXAMPLE 4

| Component | Percent by Weight |
| --- | --- |
| Stannous fluoride | 0.35 |
| Ibuprofen | 5.00 |
| White wax | 5.00 |
| Petrolatum | 89.64 |
| Peppermint oil | 0.01 |

EXAMPLE 5

| Component | Percent by Weight |
| --- | --- |
| Stannous fluoride | 0.45 |
| Allantoin | 1.00 |
| Benzocaine | 5.00 |
| White wax | 5.00 |
| Petrolatum | 88.49 |
| Peppermint oil | 0.01 |

EXAMPLE 6

| Component | Percent by Weight |
| --- | --- |
| Stannous gluconate | 4.00 |
| Polymyxin B sulfate | 0.01 |
| Benzocaine | 5.00 |
| White wax | 5.00 |
| Petrolatum | 85.98 |
| Peppermint oil | 0.01 |

EXAMPLE 7

| Component | Percent by Weight |
| --- | --- |
| Stannous gluconate | 4.00 |
| Benzocaine | 5.00 |
| Hydrocortisone | 1.00 |
| White wax | 5.00 |
| Petrolatum | 84.99 |
| Peppermint oil | 0.01 |

EXAMPLE 8

| Component | Percent by Weight |
| --- | --- |
| Stannous fluoride | 0.50 |
| Hydrocortisone | 1.00 |
| White wax | 5.00 |
| Petrolatum | 93.49 |
| Peppermint oil | 0.01 |

EXAMPLE 9

| Component | Percent by Weight |
| --- | --- |
| Stannous fluoride | 0.50 |
| Hydrocortisone | 1.00 |
| White wax | 5.00 |
| P-aminobenzoic acid | 5.00 |
| Petrolatum | 88.49 |
| Peppermint oil | 0.01 |

EXAMPLE 10

| Component | Percent by Weight |
| --- | --- |
| Stannous fluoride | 0.45 |
| Benzocaine | 5.00 |
| Polymyxin B sulfate | 0.01 |
| Hydrocortisone | 1.00 |
| White wax | 5.00 |
| Petrolatum | 89.53 |
| Peppermint oil | 0.01 |

For examples 1-10, the directions are as follows: melt the white wax in a suitable dish on a water bath, add the petrolatum, warm until liquefied, then discontinue the heating, add additional ingredients, and stir the mixture until it begins to congeal.

EXAMPLE 11

| Component | Percent by Weight |
| --- | --- |
| Stannous gluconate | 4.00 |
| Glycerin | 95.99 |
| Peppermint oil | 0.01 |

For example 11, the directions are as follows: using conventional mixing techniques, combine the stannous gluconate and glycerin. Next add the peppermint oil and mix until homogenous.

EXAMPLE 12

| Component | Percent by Weight |
| --- | --- |
| Stannous gluconate | 4.00 |
| Petrolatum | 24.91 |
| Stearyl alcohol | 25.00 |
| Propylene glycol | 12.00 |
| Sodium lauryl sulfate | 1.00 |
| Propyl paraben | 0.015 |
| Methyl paraben | 0.025 |
| Water | 33.00 |
| Peppermint oil | 0.01 |

EXAMPLE 13

| Component | Percent by Weight |
| --- | --- |
| Stannous fluoride | 0.45 |
| Benzocaine | 5.00 |
| Polymyzin B-sulfate | 0.01 |
| Stearyl alcohol | 25.00 |
| Propylene glycol | 12.00 |
| Petrolatum | 25.00 |
| Sodium lauryl sulfate | 1.00 |
| Propyl paraben | 0.015 |
| Methyl paraben | 0.025 |
| Water | 31.49 |
| Peppermint oil | 0.01 |

For examples 12 and 13, the directions are as follows: combine the stearyl alcohol, propylene glycol, petrolatum, and water. Mix thoroughly. Slowly add the stannous fluoride or stannous gluconate and sodium lauryl sulfate. If used, add the benzocaine and polymyxin B sulfate. Lastly, slowly add the propyl paraben, methyl paraben, and peppermint oil. Mix until homogenous.

What is claimed is:

1. A method for treatment of herpes virus infections in a human or lower animal subject comprising topically administering to the subject:

a. a safe and effective amount of a stannous halide selected from the group consisting of stannous bromide and stannous iodide, or a safe and effective amount of two or more stannous halides with the proviso that a combination of stannous fluoride and stannous chloride cannot be said two or more stannous halides; and b. one or more pharmaceutically acceptable carriers suitable for topical administration.

2. The method of claim 1 wherein each of the one or more stannous halides is in an amount of from about 0.05% to about 10% by weight and the pharmaceutically acceptable carrier is in an amount of from about 90% to about 99.95% by weight.

3. The method of claim 2 further comprising administering to said subject a therapeutic agent selected from the group consisting of anesthetics, analgesics, antibiotics, and combinations thereof.

* * * * *